US009915025B2

(12) United States Patent
Sworen et al.

(10) Patent No.: US 9,915,025 B2
(45) Date of Patent: Mar. 13, 2018

(54) NON-FLUORINATED MONOMERS AND POLYMERS FOR SURFACE EFFECT COMPOSITIONS

(71) Applicant: THE CHEMOURS COMPANY FC LLC, Wilmington, DE (US)

(72) Inventors: John Christopher Sworen, Chadds Ford, PA (US); Gerald Oronde Brown, Wilmington, DE (US); Tatsiana Haidzinskaya, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 136 days.

(21) Appl. No.: 14/847,161

(22) Filed: Sep. 8, 2015

(65) Prior Publication Data
US 2016/0090686 A1  Mar. 31, 2016

Related U.S. Application Data

(60) Provisional application No. 62/055,920, filed on Sep. 26, 2014.

(51) Int. Cl.
C08F 20/06 (2006.01)
C08F 20/00 (2006.01)
B32B 27/00 (2006.01)
D06M 15/263 (2006.01)
C07D 307/20 (2006.01)
C08F 122/10 (2006.01)
C08F 220/22 (2006.01)
C08F 222/10 (2006.01)
D06M 15/277 (2006.01)
C09D 133/06 (2006.01)
D21H 19/58 (2006.01)
D06M 15/233 (2006.01)
D06M 15/356 (2006.01)
D21H 19/20 (2006.01)
D21H 21/16 (2006.01)
D06M 101/06 (2006.01)
D06M 101/32 (2006.01)

(52) U.S. Cl.
CPC ......... D06M 15/263 (2013.01); C07D 307/20 (2013.01); C08F 122/105 (2013.01); C08F 220/22 (2013.01); C08F 222/1006 (2013.01); C09D 133/06 (2013.01); D06M 15/233 (2013.01); D06M 15/277 (2013.01); D06M 15/3562 (2013.01); D21H 19/20 (2013.01); D21H 19/58 (2013.01); D21H 21/16 (2013.01); C08F 2222/104 (2013.01); D06M 2101/06 (2013.01); D06M 2101/32 (2013.01); D06M 2200/01 (2013.01); D06M 2200/12 (2013.01)

(58) Field of Classification Search
CPC ............. D06M 15/277; D06M 15/233; D06M 15/263; D06M 15/3562; D06M 2101/32; D06M 2101/06; D06M 2200/01; D06M 2200/12; C08F 222/1006; C08F 220/22; C08F 220/26; C08F 122/105; C08F 2220/285; C08F 2220/282; C08F 2220/283; C08F 2222/104; C09D 3/00; D21H 19/58; C07D 307/20
USPC .................... 428/500; 526/317.1, 317, 303.1
See application file for complete search history.

(56) References Cited

U.S. PATENT DOCUMENTS

| 3,505,001 A | 4/1970 | Wagner |
| 3,907,865 A | 9/1975 | Miyata et al. |
| 4,075,411 A | 2/1978 | Dickstein |
| 4,600,761 A | 7/1986 | Ruffner et al. |
| 4,616,074 A | 10/1986 | Ruffner |
| 4,663,184 A | 5/1987 | Hegel |
| 4,859,780 A | 8/1989 | Molock et al. |
| 4,980,497 A | 12/1990 | Sasagawa et al. |
| 5,084,538 A | 1/1992 | Suzuki et al. |
| 5,104,953 A | 4/1992 | Sasagawa et al. |

(Continued)

FOREIGN PATENT DOCUMENTS

| EP | 0617061 A1 | 3/1994 |
| JP | 09050126 | 2/1997 |

(Continued)

OTHER PUBLICATIONS

International Search Report, PCT/US2015/048806, dated Dec. 7, 2015.

(Continued)

Primary Examiner — William Cheung

(57) ABSTRACT

The present invention relates to monomers and polymers of Formula (I):

$$CH_2=\overset{R^3}{\underset{|}{C}}-(\overset{O}{\underset{\|}{C}})_w-(Y-A_v-\overset{H}{\underset{|}{N}}-\overset{O}{\underset{\|}{C}})_y-X \quad (I)$$

where $R^3$ is selected from H or a $C_1$ to $C_4$ alkyl group; Y is selected from O or a substituted or unsubstituted arylene group; A is a linear or branched $C_1$ to $C_{10}$ alkylene group; w is 0 or 1; v is 0 or 1; y is 0 or 1; X is the residue of a cyclic or acyclic sugar alcohol which is substituted with at least one —$R^1$; —C(O)$R^1$; —(CH$_2$CH$_2$O)$_n$(CH(CH$_3$)CH$_2$O)$_m$R$^2$; —(CH$_2$CH$_2$O)$_n$(CH(CH$_3$)CH$_2$O)$_m$C(O)R$^1$; each n is independently 0 to 20; each m is independently 0 to 20; each $R^1$ is independently a linear or branched alkyl group having 9 to 29 carbons optionally comprising at least 1 unsaturated bond; and each $R^2$ is independently —H, a linear or branched alkyl group having 6 to 30 carbons optionally comprising at least 1 unsaturated bond, or mixtures thereof.

20 Claims, No Drawings

(56) References Cited

U.S. PATENT DOCUMENTS

| | | |
|---|---|---|
| 5,145,927 A | 9/1992 | Suzuki et al. |
| 5,393,607 A | 2/1995 | Kawasaki et al. |
| 5,866,657 A | 2/1999 | Tominaga |
| 5,869,732 A | 2/1999 | Nishikawa et al. |
| 5,891,935 A | 4/1999 | Schneider |
| 6,864,312 B2 | 3/2005 | Moore |
| 6,960,079 B2 | 11/2005 | Brennan et al. |
| 7,041,711 B2 | 5/2006 | Kunita |
| 7,205,073 B2 | 4/2007 | Kim et al. |
| 7,344,758 B2 | 3/2008 | Franchina et al. |
| 7,794,917 B2 | 9/2010 | Mori et al. |
| 8,283,095 B2 | 10/2012 | Ikeda et al. |
| 8,389,769 B2 | 3/2013 | Loccufler et al. |
| 8,445,581 B2 | 5/2013 | Gunatillake et al. |
| 2002/0045689 A1 | 4/2002 | Henry et al. |
| 2004/0170922 A1 | 9/2004 | Goto |
| 2006/0052556 A1 | 3/2006 | Franchina et al. |
| 2007/0167601 A1 | 7/2007 | Rukavina |
| 2012/0016050 A1 | 1/2012 | Leon et al. |
| 2012/0329905 A1 | 12/2012 | Nunez et al. |
| 2013/0052584 A1 | 2/2013 | Iwai |
| 2013/0288066 A1 | 10/2013 | Reiners |

FOREIGN PATENT DOCUMENTS

| | | |
|---|---|---|
| JP | 2921065 | 7/1999 |
| JP | 2003105227 | 4/2003 |
| JP | 20055179402 | 7/2005 |
| JP | 5260093 | 9/2009 |
| WO | 2000040662 A1 | 7/2000 |
| WO | WO 00/40662 * | 7/2000 |
| WO | 2000069393 A1 | 11/2000 |
| WO | 2008022985 A1 | 2/2008 |
| WO | 2009025043 A1 | 2/2009 |

OTHER PUBLICATIONS

Jeong et al., Applied Biochemistry and Biotechnology, vol. 129-132, 2006 265-276.
Jeong et al., Biochemical Engineering Journal, 29, 2006, 69-74.
Salit et al, Nauchi. Tri., Tashtentsk. Gos Univ. 1964, No. 263, 122-126, (Abstract Only).

* cited by examiner

NON-FLUORINATED MONOMERS AND POLYMERS FOR SURFACE EFFECT COMPOSITIONS

FIELD OF INVENTION

This invention relates to non-fluorinated monomers derived from sugar alcohols, and polymers and copolymers made therefrom.

BACKGROUND OF THE INVENTION

Various compositions are known to be useful as treating agents to provide water repellency and optionally stain release to textile substrates. Many such treating agents are fluorinated polymers and copolymers, or non-fluorinated polymers and copolymers. Non-fluorinated compounds are predominately polyacrylate-based or urethane-based copolymers.

Fluorinated copolymers provide good repellency to water and oil. Various attempts have been made to produce a non-fluorinated water repellent. Non-fluorinated copolymers are known to provide water repellency and optionally stain release to textiles, but are less effective than the fluorinated counterparts.

Franchina et al., in U.S. Pat. No. 7,344,758, disclose acrylic polymer extender compositions, which may be fluorinated or non-fluorinated, for use with fluorochemical repellents. These polymer extender compositions are combined with a fluorinated agent to improve the surface effects of the fluorinated treating agent.

Moore, in U.S. Pat. No. 6,864,312, discloses a polyurethane polymer that provides moisture resistance. Moore claims polyurethane polymer particle dispersions, where the polyurethane polymers are isocyanate-terminated prepolymers prepared from a formulation including a polyisocyanate and a polyol.

SUMMARY OF INVENTION

The need exists for non-fluorinated compositions that provide water repellency and optionally stain release for textiles, with performance results comparable to fluorinated treating agents. Also desirable is a non-fluorinated composition that can be bio-based derived. The present invention meets these needs.

In one embodiment, the present invention is a compound of Formula (I):

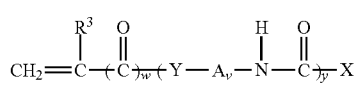

(I)

where $R^3$ is selected from H or a $C_1$ to $C_4$ alkyl group; Y is selected from O, a substituted arylene group, or an unsubstituted arylene group; A is a linear or branched $C_1$ to $C_{10}$ alkylene group; w is 0 or 1; v is 0 or 1; y is 0 or 1; provided that w+y is 1 or 2; if w is 0 then Y is a substituted or unsubstituted arylene group; and if Y is O then v is 1; X is the residue of a cyclic or acyclic sugar alcohol which is substituted with at least one —$R^1$, —$C(O)R^1$, —$(CH_2CH_2O)_n(CH(CH_3)CH_2O)_mR^2$, —$(CH_2CH_2O)_n(CH(CH_3)CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 9 to 29 carbons optionally comprising at least 1 unsaturated bond; and each $R^2$ is independently —H, a linear or branched alkyl group having 6 to 30 carbons optionally comprising at least 1 unsaturated bond, or mixtures thereof.

In another embodiment, the invention relates to a method of preparing a compound comprising reacting (a) a compound selected from Formula (III)

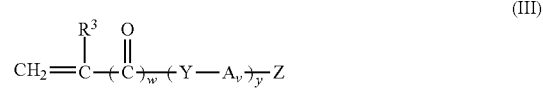

(III)

and (b) at least one cyclic or acyclic sugar alcohol which is substituted with at least one —$R^1$, —$C(O)R^1$, —$(CH_2CH_2O)_n(CH(CH_3)CH_2O)_mR^2$, —$(CH_2CH_2O)_n(CH(CH_3)CH_2O)_mC(O)R^1$, or mixtures thereof; where Y is selected from O, a substituted arylene group, or an unsubstituted arylene group; A is a linear or branched $C_1$ to $C_{10}$ alkylene group; $R^3$ is selected from H or a $C_1$ to $C_4$ alkyl group; w is 0 or 1; v is 0 or 1; y is 0 or 1; Z is selected from a halide, —$OC(O)CR^3=CH_2$, —OH, or —$NH_2$ when y is 0 and Z is —NCO when y is 1; provided that w+y is 1 or 2; if w is 0 then Y is a substituted or unsubstituted arylene group; and if Y is O then v is 1; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 9 to 29 carbons optionally comprising at least 1 unsaturated bond; and each $R^2$ is independently —H, a linear or branched alkyl group having 6 to 30 carbons optionally comprising at least 1 unsaturated bond, or mixtures thereof.

In a third embodiment, the present invention is a polymer compound comprising the repeat unit of Formula (V):

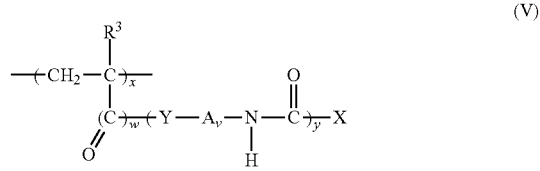

(V)

wherein $R^3$ is selected from H or a $C_1$ to $C_4$ alkyl group; x is an integer from 1 to 200; Y is selected from O, a substituted arylene group, or an unsubstituted arylene group; A is a linear or branched $C_1$ to $C_{10}$ alkylene group; w is 0 or 1; v is 0 or 1; y is 0 or 1; provided that w+y is at least 1; if w is 0 then Y is a substituted or unsubstituted arylene group; and if Y is O then v is 1; X is the residue of a cyclic or acyclic sugar alcohol which is substituted with at least one —$R^1$, —$C(O)R^1$, —$(CH_2CH_2O)_n(CH(CH_3)CH_2O)_mR^2$, —$(CH_2CH_2O)_n(CH(CH_3)CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 9 to 29 carbons optionally comprising at least 1 unsaturated bond; and each $R^2$ is independently —H, a linear or branched alkyl group having 6 to 30 carbons optionally comprising at least 1 unsaturated bond, or mixtures thereof.

DETAILED DESCRIPTION OF INVENTION

Herein all trademarks are designated with capital letters.

The present invention comprises non-fluorinated ethylenically unsaturated monomers and aqueous non-fluorinated organic polymer compositions useful for imparting durable water repellency and optionally stain release to textiles, the monomers derived from sugar alcohols. These non-fluorinated compounds provide increased durable water repellency and optionally stain release to textiles and are comparable to several fluorinated water repellent compounds.

In one embodiment, the present invention is a compound of Formula (I):

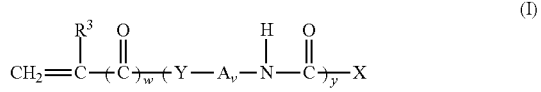

(I)

where $R^3$ is selected from H or a $C_1$ to $C_4$ alkyl group; Y is selected from O, a substituted arylene group, or an unsubstituted arylene group; A is a linear or branched $C_1$ to $C_{10}$ alkylene group; w is 0 or 1; v is 0 or 1; y is 0 or 1; provided that w+y is 1 or 2; if w is 0 then Y is a substituted or unsubstituted arylene group; and if Y is O then v is 1; X is the residue of a cyclic or acyclic sugar alcohol which is substituted with at least one —$R^1$; —$C(O)R^1$; —$(CH_2CH_2O)_n(CH(CH_3)CH_2O)_mR^2$; —$(CH_2CH_2O)_n(CH(CH_3)CH_2O)_mC(O)R^1$; or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 9 to 29 carbons optionally comprising at least 1 unsaturated bond; and each $R^2$ is independently —H, a linear or branched alkyl group having 6 to 30 carbons optionally comprising at least 1 unsaturated bond, or mixtures thereof. The term "residue of a cyclic or acyclic sugar alcohol" is herein defined as the molecular structure of a cyclic or acyclic sugar alcohol when one or more H atoms has been removed from a hydroxyl group —OH. In Formula (I), the bond of X to C=O forms an ester functional group (y=0) or urethane functional group (y=1).

The ester or urethane functional groups may be formed by any suitable method, including by reacting an ethylenically unsaturated monomer having a carboxylic acid, acyl halide, amide, isocyanate, diisocyanate, or polyisocyanate functional group with a cyclic or acyclic sugar alcohol which is substituted with at least one —$R^1$; —$C(O)R^1$; —$(CH_2CH_2O)_n(CH(CH_3)CH_2O)_mR^2$; —$(CH_2CH_2O)_n(CH(CH_3)CHO)_mC(O)R^1$; or mixtures thereof. The invention also relates to a method of preparing a compound comprising reacting (a) a compound selected from Formula (III)

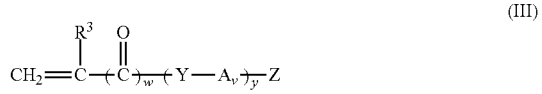

(III)

and (b) at least one cyclic or acyclic sugar alcohol which is substituted with at least one —$R^1$, —$C(O)R^1$, —$(CH_2CH_2O)_n(CH(CH_3)CH_2O)_mR^2$, —$(CH_2CH_2O)_n(CH(CH_3)CH_2O)_mC(O)R^1$, or mixtures thereof; where Y is selected from O, a substituted arylene group, or an unsubstituted arylene group; A is a linear or branched $C_1$ to $C_{10}$ alkylene group; $R^3$ is selected from H or a $C_1$ to $C_4$ alkyl group; w is 0 or 1; v is 0 or 1; y is 0 or 1; Z is selected from a halide, —$OC(O)CR^3$=$CH_2$, —OH, or —$NH_2$ when y is 0 and Z is —NCO when y is 1; provided that w+y is 1 or 2; if w is 0 then Y is a substituted or unsubstituted arylene group; and if Y is O then v is 1; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 9 to 29 carbons optionally comprising at least 1 unsaturated bond; and each $R^2$ is independently —H, a linear or branched alkyl group having 6 to 30 carbons optionally comprising at least 1 unsaturated bond, or mixtures thereof.

The cyclic or acyclic sugar alcohol is selected from a saccharide, reduced sugar, aminosaccharide, aldonic acid, or aldonic acid lactone, and is substituted with at least one —$R^1$; —$C(O)R^1$; —$(CH_2CH_2O)_n(CH(CH_3)CH_2O)_mR^2$; —$(CH_2CH_2O)_n(CH(CH_3)CH_2O)_mC(O)R^1$; or mixtures thereof. Such a substitution lends hydrophobic character to the monomer, and to the polymer molecules. In one embodiment, the cyclic or acyclic sugar alcohol is substituted with at least two —$R^1$; —$C(O)R^1$; —$(CH_2CH_2O)_n(CH(CH_3)CH_2O)_mR^2$; —$(CH_2CH_2O)_n(CH(CH_3)CH_2O)_mC(O)R^1$; or mixtures thereof; and in another embodiment, it is substituted with at least three —$R^1$; —$C(O)R^1$; —$(CH_2CH_2O)_n(CH(CH_3)CH_2O)_mR^2$; —$(CH_2CH_2O)_n(CH(CH_3)CH_2O)_mC(O)R^1$; or mixtures thereof. Examples of such sugar alcohols include but are not limited to aldoses and ketoses such as those compounds derived from tetroses, pentoses, hexoses, and heptoses. Specific examples include glucose, glyceraldehyde, erythrose, arabinose, ribose, arabinose, allose, altrose, mannose, xylose, lyxose, gulose, glactose, talose, fructose, ribulose, mannoheptulose, sedohelptulose, threose, erythritol, threitol, glucopyranose, mannopyranose, talopyranose, allopyranose, altropyranose, idopyranose, gulopyranose, glucitol, mannitol, erythritol, sorbitol, arabitol, xylitol, ribitol, galactitol, fucitol, iditol, inositol, pentaerythritol, dipenaerythritol, volemitol, gluconic acid, glyceric acid, xylonic acid, galactaric acid, ascorbic acid, citric acid, gluconic acid lactone, glyceric acid lactone, xylonic acid lactone, glucosamine, galactosamine, or mixtures thereof.

The cyclic or acyclic sugar alcohols are substituted with at least one —$R^1$; —$C(O)R^1$; —$(CH_2CH_2O)_n(CH(CH_3)CH_2O)_mR^2$; or —$(CH_2CH_2O)_n(CH(CH_3)CH_2O)_mC(O)R^1$ by any suitable method, including esterification with a fatty acid, to form hydroxy-functional substituted sugar alcohols. In one embodiment, the fatty acid substitution of the cyclic or acyclic sugar alcohols has a melting point of at least −59° C. In another embodiment, the fatty acid substitution of the cyclic or acyclic sugar alcohols has a melting point of at least 0° C., and in a third embodiment, the fatty acid substitution of the cyclic or acyclic sugar alcohols has a melting point of at least 40° C. Suitable fatty acids include, but are not limited to, caprylic acid, capric acid, lauric acid, mysteric acid, palmitic acid, stearic acid, arachidic acid, behenic acid, lignoceric acid, palmitoleic acid, lineolic acid, oleic acid, erucic acid, and mixtures thereof. In one embodiment, $R^1$ is a linear or branched alkyl group having 11 to 29 carbons, and in another embodiment, $R^1$ is a linear or branched alkyl group having 17 to 21 carbons. In one embodiment, $R^2$ is a linear or branched alkyl group having 12 to 30 carbons, in another embodiment, $R^2$ is a linear or branched alkyl group having 18 to 30 carbons, and in another embodiment, $R^2$ is a linear or branched alkyl group having 18 to 22 carbons.

In one embodiment, X is selected from Formulas (IIa), (IIIb), or (IIc):

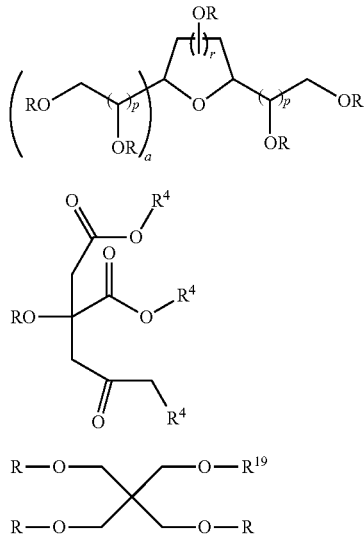

(IIa)

(IIb)

(IIc)

wherein each R is independently a direct bond to C═O of Formula I, —H, —$R^1$, —C(O)$R^1$, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$; n and m are defined as above; m+n is greater than 0; r is 1 to 3; a is 0 or 1; p is independently chosen from 0 to 2; provided that a is 0 when r is 3; each $R^1$ and $R^2$ are defined as above; provided when X is Formula (IIa), then one R is a direct bond to C═O of Formula 1; and at least one R is a —$R^1$, —C(O)$R^1$, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$; each $R^4$ is independently a direct bond to C═O of Formula I; —H, a linear or branched alkyl group having 10 to 30 carbons optionally comprising at least 1 unsaturated bond or combinations thereof, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$; provided when X is Formula (IIIb), then one R or $R^4$ is a direct bond to C═O of Formula 1; and at least one R or $R^4$ is a linear or branched alkyl group optionally comprising at least 1 unsaturated bond or combinations thereof, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$; and each $R^{19}$ is a direct bond to C═O of Formula I, —H, —C(O)$R^1$, or —CH$_2$C[CH$_2$OR]$_3$, provided when X is Formula (IIc), then one $R^{19}$ or R is a direct bond to C═O of Formula I; and at least one $R^{19}$ or R is —C(O)$R^1$, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$. In Formulas (IIa), (IIIb), or (IIc), the —(CH$_2$CH$_2$O)— represents oxyethylene groups (EO) and —(CH(CH$_3$)CH$_2$O)— represents oxypropylene groups (PO). These compounds can contain only EO groups, only PO groups, or mixtures thereof. These compounds can also be present as a tri-block copolymer designated PEG-PPG-PEG (polyethylene glycol-polypropylene glycol-polyethylene glycol), for example. In this case, X is formed by compounds (b) where the at least one cyclic or acyclic sugar alcohol which is substituted is selected from formula (IVa), (IVb), or (IVc):

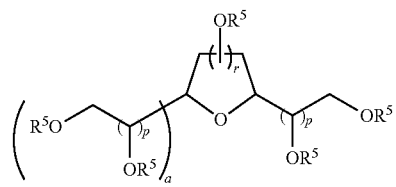

(IVa)

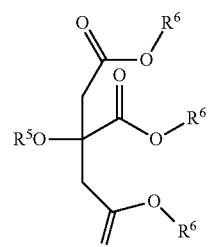

(IVb)

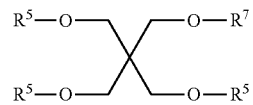

(IVc)

wherein each $R^5$ is independently —H, —$R^1$, —C(O)$R^1$, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$; n and m are defined as above; m+n is greater than 0; r is 1 to 3; a is 0 or 1; p is independently chosen from 0 to 2; provided that a is 0 when r is 3; each $R^1$ and $R^2$ are defined as above; provided when a compound of Formula (IVa) is used, then at least one $R^5$ is a —$R^1$, —C(O)$R^1$, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$; each $R^6$ is independently —H, a linear or branched alkyl group having 10 to 30 carbons optionally comprising at least 1 unsaturated bond or combinations thereof, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$; provided when a compound of Formula (IVb) is used, then at least one $R^5$ or $R^6$ is a linear or branched alkyl group optionally comprising at least 1 unsaturated bond, or combinations thereof, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$; and each $R^7$ is —H, —C(O)$R^1$, or —CH$_2$C[CH$_2$OR$^5$]$_3$, provided when a compound of Formula (IVc) is used, then at least one $R^7$ or $R^5$ is —C(O)$R^1$, —(CH$_2$CH$_2$O)$_n$(CH(CH$_3$)CH$_2$O)$_m$$R^2$, or —(CH$_2$CH$_2$O)$_n$(CH(CH$_3$)CH$_2$O)$_m$C(O)$R^1$.

Where X is Formula (IIa), any suitable substituted reduced sugar alcohol may (b) be employed, including esters of 1,4-sorbitan, esters of 2,5-sorbitan, and esters of 3,6-sorbitan. In one embodiment, X is selected from Formula (IIa) to be Formula (IIa'):

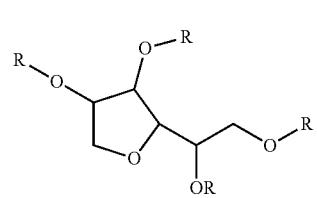

(IIa')

wherein R is further limited to independently a direct bond to C═O, —H, —$R^1$, or —C(O)$R^1$. In one embodiment, at least one R is —C(O)$R^1$ or $R^1$. Compounds (b) used to form residues of Formula (IIa'), having at least one of R as —H and at least one R selected from —C(O)R$^1$, are commonly known as alkyl sorbitans. These sorbitans can be mono-substituted, di-substituted, or tri-substituted with —C(O)R$^1$. It is known that commercially available sorbitans, such as SPAN, contain a mixture of the various sorbitans ranging from where each R is H (un-substituted), and sorbitans where each R is —C(O)R$^1$ (fully substituted); wherein R$^1$ is a linear or branched alkyl group having 9 to 29 carbons; and mixtures of various substitutions thereof. The commercially available sorbitans may also include amounts of sorbitol, isosorbide, or other intermediates or byproducts.

In one embodiment, at least one R is —C(O)R$^1$, and R$^1$ is a linear branched alkyl group having 9 to 29 carbons. Preferred compounds (b) used to form these residues include mono-, di-, and tri-substituted sorbitans derived from caprylic acid, capric acid, lauric acid, mysteric acid, palmitic acid, stearic acid, arachidic acid, behenic acid, lignoceric acid, and mixtures thereof. Particularly preferred compounds used to form X include mono-, di-, and tri-substituted sorbitan stearates or sorbitan behenins.

Optionally, R$^1$ is a linear or branched alkyl group having 9 to 29 carbons comprising at least 1 unsaturated bond. Examples of compounds (b) used to form residues of Formula (IIa') wherein at least one R is selected from —C(O)R$^1$; and R$^1$ contains least 1 unsaturated bond, include, but are not limited to, sorbitan trioleate (i.e., wherein R$^1$ is —C$_7$H$_{14}$CH=CHC$_8$H$_{17}$). Other examples include but are not limited to mono-, di-, and tri-substituted sorbitans derived from palmitoleic acid, lineolic acid, arachidonic acid, and erucic acid.

In one embodiment, X of Formula (IIa') is employed, wherein R is further limited to independently a direct bond to C=O, —H, —(CH$_2$CH$_2$O)$_n$(CH(CH$_3$)CH$_2$O)$_m$R$^2$, or —(CH$_2$CH$_2$O)$_n$(CH(CH$_3$)CH$_2$O)$_m$C(O)R$^1$. In this embodiment, at least one R is independently —(CH$_2$CH$_2$O)$_n$(CH(CH$_3$)CH$_2$O)$_m$R$^2$ or —(CH$_2$CH$_2$O)$_n$(CH(CH$_3$)CH$_2$O)$_m$C(O)R$^1$. Compounds (b) forming X of Formula (IIa'), wherein at least one R is —(CH$_2$CH$_2$O)$_n$(CH(CH$_3$)CH$_2$O)$_m$R$^2$ or —(CH$_2$CH$_2$O)$_n$(CH(CH$_3$)CH$_2$O)$_m$C(O)R$^1$, wherein each m is independently 0 to 20, each n is independently 0 to 20, and n+m is greater than 0 are known as polysorbates and are commercially available under the tradename TWEEN. These polysorbates can be mono-substituted, di-substituted, or tri-substituted with alkyl groups R$^1$ or R$^2$. It is known that commercially available polysorbates contain a mixture of the various polysorbates ranging from where each R$^2$ is H (unsubsituted), and polysorbates where each R$^1$ is a linear or branched alkyl group having 9 to 29 carbons (fully substituted); and mixtures of various substitutions thereof. Examples of compounds used to form X of Formula (IIa') include polysorbates such as polysorbate tristearate, and polysorbate monostearate. Examples of compounds (b) used to form X of Formula (IIa') wherein m+n is greater than 0, and wherein R$^1$ comprises at least 1 unsaturated bond, include but are not limited to, polysorbate trioleate (wherein R$^1$ is C$_7$H$_{14}$CH=CHC$_8$H$_{17}$), are sold commercially under the name Polysorbate 80. Reagents may include mixtures of compounds having various values for R, R$^1$, and R$^2$, and may also include mixtures of compounds where R$^1$ comprises at least one unsaturated bond with compounds where R$^1$ is fully saturated. In one aspect, R$^2$ is H, and m is a positive integer.

In one embodiment, X is selected from Formula (IIIb). Compounds (b) used to form X of Formula (IIb) are known as alkyl citrates. These citrates can be present as a mono-substituted, di-substituted, or tri-substituted compound with alkyl groups. It is known that commercially available citrates contain a mixture of the various citrates as well as citric acids from where R and each R$^4$ is —H, ranging to citrates where each R$^4$ is a linear or branched alkyl group having 10 to 30 carbons optionally comprising at least 1 unsaturated bond; and mixtures of various substitutions thereof. Mixtures of citrates having various values for R$^1$, R$^2$, and R$^4$ may be used, and may also include mixtures of compounds where R$^1$ comprises at least one unsaturated bond with compounds where R$^1$ is fully saturated. Alkyl citrates are also commercially available wherein m+n is greater than 0, R$^4$ is —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$ and are present in the various substitutions from wherein R and each R$^2$ is H to wherein each R$^1$ and/or R$^2$ is a linear or branched alkyl group having 5 to 30 carbons optionally comprising at least 1 unsaturated bond. Examples of compounds used to form X of Formula (IIb) include, but are not limited to, trialkyl citrates.

In one embodiment, X is selected from Formula (IIc). Compounds (b) used to form X of Formula (IIc) are known as pentaerythriol esters. These pentaerythriol esters can be present as a mono-substituted, di-substituted, or tri-substituted with alkyl groups. Preferred compounds used to form X of Formula (IIc) are dipentaerythritol esters, where R$^{19}$ is —CH$_2$C[CH$_2$OR]$_3$. It is known that commercially available pentaerythriol esters contain a mixture of the various pentaerythriol esters where R$^{19}$ and each R is —H, ranging to pentaerythriol esters where each R is —C(O)R$^1$, and R$^1$ is a linear or branched alkyl group having 9 to 29 carbons optionally comprising at least 1 unsaturated bond; and mixtures of various substitutions thereof. The pentaerythriol esters also may contain compounds with mixtures of different chain lengths for R, or mixtures of compounds where R$^1$ comprises at least one unsaturated bond with compounds where R$^1$ is fully saturated.

Compound (b) and residue X of Formulas (IIa), (IIIb), and (IIc) can all be bio-based derived. By "bio-based derived", it is meant that at least 10% of the material can be produced from non-crude oil sources, such as plants, other vegetation, and tallow. In one embodiment, X is from about 10% to 100% bio-based derived. In one embodiment, X is from about 35% to 100% bio-based derived. In another embodiment, X is from about 50% to 100% bio-based derived. In one embodiment, X is from about 75% to 100% bio-based derived. In one embodiment, X is 100% bio-based derived. The average OH value of the substituted sugar alcohol compounds used to form X can range from just greater than 0 to about 230. In one embodiment, the average OH value is from about 10 to about 175, and in another embodiment, the average OH value is from about 25 to about 140.

In one embodiment, Formula (I) is chosen such that w is 1 and y is 0. Such a compound can be formed by reacting compound (b) at least one cyclic or acyclic sugar alcohol which is substituted with at least one R$^1$, —C(O)R$^1$, —(CH$_2$CH$_2$O)$_n$(CH(CH$_3$)CH$_2$O)$_m$R$^2$, or —(CH$_2$CH$_2$O)$_n$(CH(CH$_3$)CH$_2$O)$_m$C(O)R$^1$ with a compound (a) of Formula (III), where w is 1, y is 0, and Z is selected from a halide, —OC(O)CR$^3$=CH$_2$, —OH, or —NH$_2$. For example, the alcohol compound (b) may be combined with triethylamine in solvent, followed by a gradual addition of acryloyl chloride or methacryloyl chloride. The solid is removed, typically by filtration, and washed with organic solvent, and then purified, usually by extraction and water-washing, concentrating and drying under vacuum. In another method, compounds of the invention can be prepared from the substituted sugar alcohols (b) by reacting with acrylamide or acrylic, methacrylic or chloroacrylic acid in the presence of an acid catalyst, such as toluenesulfonic acid, and a solvent, such as hexane, cyclohexane, heptane, octane, or toluene. The organic layer is washed with water, isolated, and then purified, typically by vacuum distillation. Optionally, inhibitors such as 4-methoxyphenol may be added during or after synthesis.

In another embodiment, Formula (I) is chosen such that w is 1, y is 1, and Y is O. Such a compound can be formed by reacting compound (b) with a compound (a) of Formula (III), where w is 1, y is 1, Y is O, and Z is —NCO. Any isocyanate compound fitting this formula may be used, and the inventive compound may be synthesized using conventional urethane synthesis techniques. In one further embodiment, Formula (I) is chosen such that w is 0, y is 1, and Y is a substituted or unsubstituted arylene group. Such a compound may be formed by reacting compound (b) with a compound (a) of Formula (III), where w is 0, y is 1, Y is a substituted or unsubstituted arylene group, and Z is —NCO. Any isocyanate compound fitting this formula may be used, including but not limited to substituted or unsubstituted styrene isocyanates. The inventive compounds may be synthesized using conventional urethane synthesis techniques. For example, the isocyanate compound (a) may be combined with the substituted sugar alcohol compound (a) and a catalyst in organic solvent, heating with stirring until the solution tests negative for active isocyanate groups, and collected.

In one embodiment, the invention relates to a mixture of compounds of Formula (I). In addition to compounds of the present invention as described herein, these compositions may also comprise additional compounds that are present from commercially available sorbitans, polysorbates, alkyl citrates, or pentaerythritols. These compounds can be present as a mixture of the various substituted sugar alcohols from fully unsubstituted to fully substituted, and the various substitutions in between, and optionally, the linear or branched alkyl group having 9 to 29 carbons comprises at least 1 unsaturated bond.

In another aspect, the invention relates to a polymer compound comprising the repeat unit of Formula (V):

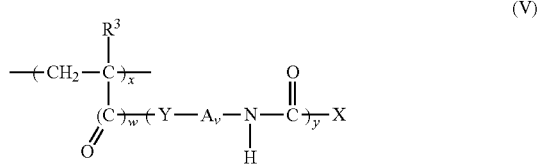

(V)

wherein $R^3$ is selected from H or a $C_1$ to $C_4$ alkyl group; x is an integer from 1 to 200; Y is selected from O, a substituted arylene group, or an unsubstituted arylene group; A is a linear or branched $C_1$ to $C_{10}$ alkylene group; w is 0 or 1; v is 0 or 1; y is 0 or 1; provided that w+y is at least 1; if w is 0 then Y is a substituted or unsubstituted arylene group; and if Y is O then v is 1; X is the residue of a cyclic or acyclic sugar alcohol which is substituted with at least one —$R^1$, —C(O)$R^1$, —(CH$_2$CH$_2$O)$_n$(CH(CH$_3$)CH$_2$O)$_m$$R^2$, —(CH$_2$CH$_2$O)$_n$(CH(CH$_3$)CH$_2$O)$_m$C(O)$R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 9 to 29 carbons optionally comprising at least 1 unsaturated bond; and each $R^2$ is independently —H, a linear or branched alkyl group having 6 to 30 carbons optionally comprising at least 1 unsaturated bond, or mixtures thereof. Compositions comprising such polymer compounds may be in form of an aqueous dispersion or aqueous emulsion, and may further comprise a solvent selected from organic solvents. The polymer compounds may be in the form of homopolymers or copolymers, and may be completely non-fluorinated or may be partially fluorinated by the copolymerization with one or more fluorinated monomers. They may have a number average molecular weight of 5000 to 200,000. In one embodiment, the polymers have a number average molecular weight of 50,000 to 200,000.

When the polymer compound is a copolymer, the polymers further comprise at least one repeat unit from an ethylenically unsaturated monomer having a functional group selected from a linear or branched hydrocarbon, linear or branched fluorocarbon, ether, alcohol, anhydride, oxyalkylene, ester, formate, carboxylic acid, carbamate, urea, amine, amide, sulfonate, sulfonic acid, sulfonamide, halide, saturated or unsaturated cyclic hydrocarbon, morpholine, pyrrolidine, piperidine, or mixtures thereof.

The ethylenically unsaturated monomer can be any monomer having an ethylenically unsaturated bond with a functional group described above, including but not limited to linear or branched alkyl (meth)acrylates, amino and diamino (meth)acrylates, linear or branched fluoroalkyl (meth)acrylates optionally interrupted by O, CH$_2$, CH$_2$CH$_2$, or SO$_2$NH, alkoxylated (meth)acrylates, (meth)acylic acid, vinyl or vinylidene chloride, glycidyl (meth)acrylate, vinyl acetate, hydroxyalkylene (meth)acrylate, urethane or urea (meth) acrylates, (meth)acrylamides including N-methyloyl (meth) acrylamide, alkoxyalkyl (meth)acrylamide, styrene, alpha-methylstyrene, chloromethyl-substituted styrene, ethylenediol di(meth)acrylate, 2-acrylamido-2-methyl-1-propane sulfonic acid (AMPS), and maleic anhydride. Suitable monomers include those listed above but also include other ethylenically unsaturated monomers that have been shown useful in hydrophobic polymers for fibrous substrates.

Specific fluorinated ethylenically unsaturated monomers used to incorporate fluoroalkyl functionality include but are not limited to $R_fCH_2CH_2OC(O)CR^3$=$CH_2$, $R_fSO_2NHCH_2CH_2OC(O)CR^3$=$CH_2$, $R_fCH_2CH_2SCH_2CH_2OC(O)CR^3$=$CH_2$, $R_fCH_2CH_2CF_2CF_2CH_2CH_2OC(O)CR^3$=$CH_2$, $R_fCH_2CH_2(CF_2CF_2CH_2CH_2)_2OC(O)CR^3$=$CH_2$, $R_fCH_2CF_2CH_2CH_2OC(O)CR^3$=$CH_2$, $R_fCH_2CF_2CH_2CF_2CH_2CH_2OC(O)CR^3$=$CH_2$, $R_fOCF_2CF_2CH_2CH_2OC(O)CR^3$=$CH_2$, $R_fCH_2OCH_2CH_2OC(O)CR^3$=$CH_2$, $R_fCHFCH_2CH_2OH$, $R_fCH_2O(CH_2)_6OC(O)CR^3$=$CH_2$, $(CF_3)_2CFCH_2CH_2OC(O)CR^3$=$CH_2$, $(CF_3)_2CFCH_2CH_2CH_2OC(O)CR^3$=$CH_2$, $R_fCH_2CH_2SO_2NHCH_2CH_2OC(O)CR^3$=$CH_2$, $R_fCH_2CH_2SO_2N(CH_3)CH_2CH_2OC(O)CR^3$=$CH_2$, $R_fCH_2CH_2SO_2N(CH_2CH_3)CH_2CH_2OC(O)CR^3$=$CH_2$, $R$—$(CF(CF_3)CF_2O)_yCH_2OC(O)CR^3$=$CH_2$, $CF_2$=$CFOCF_2CF(CF_3)OCF_2CF_2CH_2OC(O)CR^3$=$CH_2$, or $R_fCH_2OC_2F_4CH_2OCH_2CH_2OC(O)CR^3$=$CH_2$, where $R_f$ is a linear or branched fluoroalkyl of $C_1$-$C_{20}$, or $CH_2$=$CH$—COO—$C_2H_4$—N(CH$_3$)—SO$_2$—$C_2H_4$—$C_6F_{13}$, 2-[methyl [(3,3,4,4,5,5,6,6,6-nonfluorohexyl)sulfonyl]amino]ethyl acrylate, 2-[methyl[(3,3,4,4,5,5,6,6,7,7,8,8,8-tridecafluorooctyl)sulfonyl]amino]ethyl methacrylate, or 2-[[(3,3,4,4,5,5,6,6,7,7,8,8,8-tridecafluorooctyl)sulfonyl]amino]ethyl methacrylate. In one embodiment, $R_f$ is a $C_2$ to $C_6$ perfluoroalkyl.

The polymers can be synthesized by any means known to one skilled in the art. For example, the monomer or monomers are contacted in a solvent system, such as isopropyl alcohol and/or methyl isobutyl ketone, with a polymerization initiator, the mixture is heated to the activation temperature of the initiator, and the polymerization is allowed to propagate. The polymer mixture can then be contacted with an aqueous, and the organic solvents are removed, such as by distillation. The final product is an aqueous dispersion or emulsion.

When a comonomer selected from Formula (VIa) or Formula (VIb),

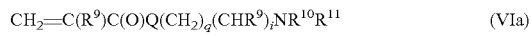

$$CH_2=C(R^9)C(O)Q(CH_2)_q(CHR^9)_iNR^{10}R^{11} \quad (VIa)$$

$$CH_2=C(R^9)NR^{12}R^{13} \quad (VIb)$$

or a mixture thereof, is used, wherein $R^9$ is independently selected from H or $CH_3$; $R^{10}$ and $R^{11}$ are each independently $C_1$ to $C_4$ alkyl, hydroxyethyl, or benzyl; or $R^{10}$ and $R^{11}$ together with the nitrogen atom form a morpholine, pyrrolidine, or piperidine ring; $R^{12}$ and $R^{13}$ are each independently selected from H or $C_1$ to $C_4$ alkyl; Q is —O— or —$NR^{14}$— wherein $R^{14}$ is H or $C_1$-$C_4$ alkyl; i is 0 to 4, and q is 1 to 4, then the nitrogen bonded to $R^{10}$ and $R^{11}$ may be from about 0% to 100% salinized, quaternized, or present as an amine oxide. The copolymers of this embodiment can be synthesized by any means known to one skilled in the art. The copolymer may be optionally partially or completely salinized or quaternized by conventional techniques known to those skilled in the art. In one aspect, the degree of salinization or quaternization is from about 50% to about 100%. Preferably, the copolymers are synthesized by combining the monomers in a solvent system, such as isopropyl alcohol and methyl isobutyl ketone, heating the mixture to the activation temperature of an initiator, slowly introducing an initiator into the monomer mixture, and allowing the copolymerization to propagate. The polymer mixture can then be contacted with an aqueous salinization solution, such as acetic acid solution, and the organic solvents are removed, preferably by distillation. The final product is an aqueous emulsion.

It will be apparent to one skilled in the art that many changes to any or all of the above procedures can also be used to optimize the reaction conditions for obtaining maximum yield, productivity, or product quality. When the polymer contains repeat units of Formula (V) as well as repeat units from fluorinated monomers, Formulas (VIa), (VIb), and/or (VIc), the repeat unit (V) will compose about 15-70% by mol, the fluorinated repeat units will compose about 0-20% by mol, the repeat units from (VIa or (VIb) will compose 10-60% by mol, and the repeat units from Formula (VIc) will compose about 5-25% by mol, wherein the sum of repeat units equals 100%. In one embodiment, the repeat unit (V) will compose about 20-55% by mol, the repeat units from fluorinated repeat units will compose about 0-15% by weight, the repeat units from (VIa or (VIb) will compose 20-45% by mol, and the repeat units from Formula (VIc) will compose about 10-20% by mol, wherein the sum of repeat units equals 100%. In one embodiment, when no fluorinated repeat units are present, the repeat units of Formula (V) compose 40-100% by mol of the polymer in one aspect, 40-70% by mol of the polymer in another aspect, and 40-60% by mol in a further aspect.

The resulting polymers are useful for providing surface effects to a fibrous substrate, including water repellency and optionally stain release properties. In one embodiment, the invention is a method of treating a fibrous substrate comprising applying to the surface of a substrate a polymer of the invention. The polymer composition above is contacted with the substrate by any suitable method. Such methods include, but are not limited to, application by exhaustion, foam, flex-nip, nip, pad, kiss-roll, beck, skein, winch, liquid injection, overflow flood, roll, brush, roller, spray, dipping, immersion, and the like. The composition is also contacted by use of a beck dyeing procedure, continuous dyeing procedure or thread-line application.

The polymer of the present invention is applied to the substrate as such, or in combination with other optional textile finishes or surface treating agents. Such optional additional components include treating agents or finishes to achieve additional surface effects, or additives commonly used with such agents or finishes. Such additional components comprise compounds or compositions that provide surface effects such as no iron, easy to iron, shrinkage control, wrinkle free, permanent press, moisture control, softness, strength, anti-slip, anti-static, anti-snag, anti-pill, stain release, soil repellency, soil release, water repellency, odor control, antimicrobial, sun protection, cleanability and similar effects. Such components may be fluorinated or non-fluorinated. One or more of such treating agents or finishes are applied to the substrate before, after, or simultaneously with the composition of the present invention. For example, for fibrous substrates, when synthetic or cotton fabrics are treated, use of a wetting agent can be desirable, such as ALKANOL 6112 available from E. I. du Pont de Nemours and Company, Wilmington, Del. When cotton or cotton-blended fabrics are treated, a wrinkle-resistant resin can be used such as PERMAFRESH EFC available from Omnova Solutions, Chester, S.C.

Other additives commonly used with such treating agents or finishes are also optionally present, such as surfactants, pH adjusters, cross linkers, wetting agents, wax extenders, and other additives known by those skilled in the art. Suitable surfactants include anionic, cationic, nonionic, N-oxides and amphoteric surfactants. Examples of such additives include processing aids, foaming agents, lubricants, anti-stains, and the like. The composition is applied at a manufacturing facility, retailer location, or prior to installation and use, or at a consumer location.

Optionally, a blocked isocyanate is added with the composition of the present invention to further promote durability (i.e., as a blended composition). An example of a suitable blocked isocyanate to use in the present invention is PHOBOL XAN available from Huntsman Corp, Salt Lake City, Utah Other commercially available blocked isocyanates are also suitable for use herein. The desirability of adding a blocked isocyanate depends on the particular application for the copolymer. For most of the presently envisioned applications, it does not need to be present to achieve satisfactory cross-linking between chains or bonding to the substrate. When added as a blended isocyanate, amounts up to about 20% by weight are added.

The optimal treatment for a given substrate depends on (1) the characteristics of the compound or composition of the present invention, (2) the characteristics of the surface of the substrate, (3) the amount of compound or composition of the present invention applied to the surface, (4) the method of application of the compound or composition of the present invention onto the surface, and many other factors. Some compounds or compositions of the present invention work well on many different substrates and are repellent to water. Dispersions prepared from compounds of the present invention are generally applied to fibrous substrates by spraying, dipping, padding, or other well-known methods.

After excess liquid has been removed, for example by squeeze rolls, the treated fibrous substrate is dried and then cured by heating, for example, to from about 100° C. to about 190° C., for at least 30 seconds, typically from about 60 to about 240 seconds. Such curing enhances oil-, water- and soil repellency and durability of the repellency. While these curing conditions are typical, some commercial apparatus may operate outside these ranges because of its specific design features.

In another embodiment, the present invention is a fibrous substrate treated by contacting a fibrous substrate with the polymer described above. Suitable substrates include fibers, yarns, fabrics, fabric blends, textiles, nonwovens, paper, leather, and carpets. These are made from natural or synthetic fibers including cotton, cellulose, wool, silk, rayon, nylon, aramid, acetate, acrylic, jute, sisal, sea grass, coir, polyamide, polyester, polyolefin, polyacrylonitrile, polypropylene, polyaramid, or blends thereof. By "fabric blends" is meant fabric made of two or more types of fibers. Typically these blends are a combination of at least one natural fiber and at least one synthetic fiber, but also can include a blend of two or more natural fibers or of two or more synthetic fibers. The nonwoven substrates include, for example, spun-laced nonwovens, such as SONTARA available from E. I. du Pont de Nemours and Company, Wilmington, Del., and spunbonded-meltblown-spunbonded nonwovens. The treated substrates of the present invention have excellent water repellency and optionally stain release properties.

The treated substrates of the present invention are useful in a variety of applications and products such as clothing, protective garments, carpet, upholstery, furnishings, and other uses. The excellent surface properties described above help to maintain surface cleanliness and therefore can permit longer use.

Test Methods and Materials

All solvents and reagents, unless otherwise indicated, were purchased from Sigma-Aldrich, St. Louis, Mo., and used directly as supplied. Methyl isobutyl ketone (MIBK) and poly(ethylene glycol) methacrylate MW=360 (7-EO methacrylate) are both available from Sigma-Aldrich, St. Louis, Mo.

NUJOL is a mineral oil having a Saybolt viscosity of 360/390 s at 38° C. and a specific gravity of 0.880/0.900 g/cm3 at 15° C., available from Plough, Inc., Kenilworth, N.J.

Sorbitan tristearate are commercially available from Croda, East Yorkshire, England, or DuPont Nutrition & Health, Copenhagen, Denmark. Sorbitan trioleate is available from Croda, East Yorkshire, England.

2-Methyl-2-propenoic acid, 3,3,4,4,5,5,6,6,7,7,8,8,8-tridecafluorooctyl ester (62-FMA) and 2-propenoic acid, 3,3,4,4,5,5,6,6,7,7,8,8,8-tridecafluorooctyl ester (62-FA) are commercially available from DuPont Chemicals and Fluoroproducts, Wilmington, Del.

N-(isobutoxymethyl)methacrylamide was obtained from Polysciences, Inc., Warrington, Pa.

BLEMMER PE-350, PP-500, and PME-400 are poly(ethylene glycol) methacrylate, poly(propylene glycol) methacrylate, and poly(ethylene glycol) methyl ether methacrylate, respectively, available from NOF Corporation, Tokyo, Japan.

CHEMIDEX S is an alkanolamide surfactant, available from Lubrizol, Wickliffe, Ohio.

PHOBOL XAN was obtained from Huntsman Corp., Salt Lake City, Utah.

ETHAL LA-4 is a laureth-4 surfactant available from Ethox Chemicals, Buffalo, N.Y.

STEPOSOL SB-W is a soya methyl ester surfactant available from Stepan, Northfield, Ill.

ARMEEN DM-18D was obtained from Akzo-Nobel, Bridgewater, N.J.

BRIJ L4 is polyethylene glycol dodecyl ether available from Sigma-Aldrich, St. Louis, Mo.

The following test methods and materials were used in the examples herein.

Test Method 1—Fabric Treatment

The fabrics treated in this study were 100% by weight khaki cotton twill available from SDL Atlas Textile Testing Solutions, Rock Hill, S.C. 29732 and 100% by weight red polyester fabric available from L. Michael OY, Finland. The fabric was treated with the aqueous dispersions of various emulsion polymers using a conventional pad bath (dipping) process. The prepared concentrated dispersions were diluted with deionized water to achieve a pad bath having 60 g/L or 100 g/L of the product in the bath. For the treatment of the cotton fabric, a wetting agent, INVADINE PBN and a catalyzed cross-linking agent, KNITTEX 7636 (all available from Huntsman, Salt Lake City, Utah) were also included in the bath at 5 g/L and 30 g/L respectively. The fabric was padded in the bath, and the excess liquid was removed by squeeze rollers. The wet pickup was around 95% on the cotton substrate. The "wet pick up" is the weight of the bath solution of the emulsion polymer and additives applied to the fabric, based on the dry weight of the fabric.

The fabric was cured at approximately 165° C. for 3 minutes and allowed to "rest" after treatment and cure for at least 15 hours.

For the treatment of the polyester fabric, a wetting agent, INVADINE PBN (available from Huntsman, Charlotte, N.C., USA) and 20% acetic acid were also included in the bath at 5 g/L and 1 g/L respectively. The fabric was padded in the bath, and the excess liquid removed by squeeze rollers. The wet pickup was around 55% on the polyester substrate. The "wet pick up" is the weight of the bath solution of the emulsion polymer and additives applied to the fabric, based on the dry weight of the fabric. The fabric was cured at approximately 160° C. for 2 minutes and allowed to "rest" after treatment and cure for about 15 to about 18 hours.

Test Method 2—Water Drop

The water repellency of a treated substrate was measured according to the DuPont Technical Laboratory Method as outlined in the TEFLON Global Specifications and Quality Control Tests information packet. The test determines the resistance of a treated substrate to wetting by aqueous liquids. Drops of water-alcohol mixtures of varying surface tensions are placed on the fabric and the extent of surface wetting is determined visually. The test provides a rough index of aqueous stain resistance. The higher the water repellency rating, the better the resistance the finished substrate has to staining by water-based substances. The composition of standard test liquids is shown in the following Table 1. Ratings of 0.5 increments are determined by subtracting one half from the numbers in Table 1 for borderline passing of the test liquid.

TABLE 1

| Standard Test Liquids | | |
|---|---|---|
| Water Repellency Rating Number | Composition Vol. %, Isopropyl Alcohol | Composition, Vol. % Distilled Water |
| 1 | 2 | 98 |
| 2 | 5 | 95 |
| 3 | 10 | 90 |
| 4 | 20 | 80 |
| 5 | 30 | 70 |

TABLE 1-continued

Standard Test Liquids

| Water Repellency Rating Number | Composition Vol. %, Isopropyl Alcohol | Composition, Vol. % Distilled Water |
|---|---|---|
| 6 | 40 | 60 |
| 7 | 50 | 50 |
| 8 | 60 | 40 |
| 9 | 70 | 30 |
| 10 | 80 | 20 |
| 11 | 90 | 10 |
| 12 | 100 | 0 |

Test Method 3—Oil Repellency

The treated fabric samples were tested for oil repellency by a modification of AATCC standard Test Method No. 118, conducted as follows: A fabric sample, treated with an aqueous dispersion of polymer, was conditioned for a minimum of 15 hours at 23° C.+65% relative humidity prior to testing. A series of organic liquids, identified below in Table 2, were then applied drop wise to the fabric samples. Beginning with the lowest numbered test liquid (Repellency Rating No. 1), one drop (approximately 5 mm in diameter or 0.05 mL volume) was placed on each of three locations at least 5 mm apart. The drops were observed for 30 seconds. If, at the end of this period, two of the three drops were still spherical in shape with no wicking around the drops, three drops of the next highest numbered liquid were placed on adjacent sites and similarly observed for 30 seconds. The procedure was continued until one of the test liquids resulted in two of the three drops failing to remain spherical to hemispherical, or wetting or wicking occurred.

The oil repellency rating of the fabric was the highest numbered test liquid for which two of the three drops remained spherical to hemispherical, with no wicking for 30 seconds. Ratings of 0.5 increments were determined by subtracting one-half from the number in Table 2 for borderline passing of the next liquid. Higher ratings indicate greater repellency. The composition of oil repellency test liquids is shown in the Table 2.

TABLE 2

Oil Repellency Test Liquids

| Oil Repellency Rating | Test Solution |
|---|---|
| 1 | NUJOL Purified Mineral Oil |
| 2 | 65/35 NUJOL/n-hexadecane by volume at 21° C. |
| 3 | n-hexadecane |
| 4 | n-tetradecane |
| 5 | n-dodecane |
| 6 | n-decane |

Test Method 4—Spray Test

The dynamic water repellency of treated substrates was measured according to the American Association of Textile Chemists and Colorists (AATCC) TM-22. Samples are visually scored by reference to published standards, with a rating of 100 denoting no water penetration or surface adhesion. A rating of 90 denotes slight random sticking or wetting without penetration; lower values indicate progressively greater wetting and penetration. Test Method 2, the dynamic water repellency test, is a demanding and realistic test of water repellency.

Test Method 5—Stain Release

This test measures the ability of a fabric to release oily stains during home laundering.

Treated textiles are placed on a flat surface. Using an eyedropper, 5 drops of MAZOLA Corn Oil or mineral oil (0.2 mL) were placed onto the fabric to form 1 drop of oil. A weight (5 lb, 2.27 kg) is placed on top of the oil drop with a piece of glassine paper separating the oil drop. The weight was left in place for 60 seconds. After 60 seconds, the weight and glassine paper are removed. The textiles samples were then washed using a automatic washer high for 12 minutes with AATCC 1993 Standard Reference Detergent WOB12 or granular detergent (100 g). The textiles were then dried on high for 45-50 minutes. The textiles were then evaluated for residual stain of 1 to 5, 1 having the largest residual stain remaining and 5 being no stain residual was visible. In the examples below, stain release ratings of corn oil are designated by the term "Corn Oil", and stain release ratings of mineral oil are designated by the term "Mineral Oil".

Examples of the compounds and compositions of the instant invention can be made from various reactive ethylenically unsaturated monomers and various substituted sugar alcohols, or mixtures thereof. The present invention is not to be limited by the examples below.

Comparative Example A

Untreated fabric samples were tested according to the test methods above. Both cotton and polyester fabrics had a water drop rating of 0, an oil drop rating of 0, and a spray rating of 0.

Example 1: Synthesis of a Sorbitan Tristearate Methacrylate (M1)

$CH_2=C(CH_3)-C(O)-STS$, where STS is the Residue of Sorbitan Tristearate

A dry 1-L round bottom four neck flask was assembled with a thermocouple, mechanical stirrer, a nitrogen inlet, condenser, and gas outlet. The flask was charged with sorbitan tristearate (100 g, OH value 76, 162.57 mmol), dichloromethane (300 g), and triethylamine (17.82 g, 176.11 mmol). Methacryloyl chloride (15.79 mL, 162.57 mmol) was slowly added to the solution via syringe. The flask was insulated with foil. The reaction mixture was stirred under nitrogen at room temperature for 48 hours, at which point 200 mL of ether was added. Triethyl ammonium chloride was removed by filtration. Organic layers were washed with 5 wt % acetic acid solution (250 mL), the aqueous layer was extracted with dichloromethane, and the organic layers were washed with saturated NaHCO3 solution. The organic layers were dried with $MgSO_4$ and filtered. 0.01 g of p-methoxyphenol polymerization inhibitor was added, and organic solvent was removed via rotary evaporation without heating. The product was a light yellow solid at room temperature.

Example 2: Synthesis of a Sorbitan Tristearate Urethane Methacrylate (M2)

$CH_2=C(CH_3)-C(O)OCH_2CH_2NHC(O)-STS$, where STS is the Residue of Sorbitan Tristearate A dry 4-neck 500 mL round bottom flask was assembled with a thermocouple, mechanical stirrer, nitrogen inlet, condenser, and gas outlet. The flask was charged with 2-isocyanatoethyl methacrylate (25.0 g, 161.13 mmol), MIBK (141.44 g), and a solution of 0.50 weight % $FeCl_3$ in MIBK (2.5 g). The mixture was heated to 60° C., and sorbitan tristearate (118.94 g, OH value 76) was added to the flask. The temperature was then raised to 80° C. and stirred overnight. After 24 hours, 1,8-diazabicyclooundec-7-ene (0.05 g) was added, and the reaction mixture was stirred for another 24 hours at 80° C. When the solution tested negative for isocyanates, it was filtered through a milk filter and collected.

Example 3: Synthesis of a Sorbitan Tristearate Urethane Styrene Monomer (M3)

$CH_2$=CH—$(C_6H_4)$—$C(CH_3)_2$—NHC(O)—STS, where STS is the Residue of Sorbitan Tristearate A dry 4-neck 500 mL round bottom flask was assembled with a thermocouple, mechanical stirrer, nitrogen inlet, condenser, and gas outlet. The flask was charged with 3-isopropenyl-α,α-dimethylbenzyl isocyanate (36.0 g, 178.8 mmol), MIBK (168 g), a solution of 0.50 weight % $FeCl_3$ in MIBK (6.0 g), and 1,8-diazabicycloundec-7-ene (0.1 g). The mixture was heated to 60° C. Sorbitan tristearate (132.04 g, 178.8 mmol) was added to the flask. The temperature was then raised to 80° C. and stirred overnight. When the solution tested negative for isocyanates, it was cooled to 45° C., filtered through a milk filter, and collected.

Example 4: Synthesis of Sorbitan Trioleate Methacrylate (M4)

$CH_2$=$C(CH_3)$—C(O)—STO, where STO is the Residue of Sorbitan Trioleate

A dry 250 g round bottom flask was charged with sorbitan trioleate (50.0 g, 0.0522 mols), dichloromethane (50 mL), and triethylamine (14.6 mL). The mixture was cooled to 0° C. in an ice bath. Methacryloyl chloride (5.1 mL, 0.0522 mols) was slowly added to the solution, and the reaction mixture was stirred under nitrogen at room temperature overnight. A second portion of methacryloyl chloride (5.1 mL, 0.0522 mols) was then added, the reaction mixture was stirred at room temperature for 24 more hours, and water (100 mL) was added. The layers were separated and the aqueous layer was extracted with dichloromethane. Combined organic layers were washed with saturated $Na_2CO_3$ and water, dried with $MgSO_4$, filtered, and concentrated.

Examples 5-10

A 4-neck 500 mL round bottom flask was assembled with a glass stopper, thermocouple, mechanical stirrer, nitrogen inlet, condenser, and gas outlet. The flask was charged with monomers according to Table 3 and MIBK (to dilute monomers to about 50% by weight). The solution was sparged with nitrogen for 10 minutes and heated to 60° C. VAZO 67 initiator was added, and the reaction mixture was heated to 70° C. and stirred overnight.

In a separate flask, hot deionized water was combined with surfactants according to Table 3 and heated to 70° C. The surfactant solution was then added to the reaction flask and stirred for 30 minutes at 75° C. For example 5, the dispersion was homogenized for 4 passes at 6000 psi. For examples 6-10, the dispersions were sonicated. Organic solvent was removed via rotary evaporation. The final product was filtered through a sock filter and diluted to 20% solids. Dispersions were applied to fabric samples at 90 g/L at 20% solids which is equivalent to 3.6 g of polymer per 200 g of pad bath, with 10 g/L of PHOBOL XAN, and tested according to the test methods above.

TABLE 3

Reagents and Performance of Examples 5-10

| Example | 5 | 6 | 7 | 8 | 9 | 10 |
|---|---|---|---|---|---|---|
| Reagent Amounts (g) | | | | | | |
| M1 | 53.5 | 15.5 | 17.83 | 15.5 | 15.5 | 15.5 |
| Methacrylic Acid | — | — | — | — | — | 0.05 |
| Isobornyl Methacrylate | — | 1.00 | — | 1.00 | 3.00 | 1.00 |
| BLEMMER PE-350 | — | 0.10 | — | — | — | — |
| BLEMMER PP-500 | — | — | 7.76 | 0.30 | 0.30 | — |
| VAZO 67 | 3.2 | 1.0 | 2.3 | 1.0 | 1.1 | 1.0 |
| Surfactant Solution (g) | | | | | | |
| Water | 150 | 55 | 221 | 55 | 60 | 55 |
| ARMEEN DM-18D | 3.53 | 1.10 | 1.00 | 1.11 | 1.24 | 1.10 |
| Acetic Acid | 2.22 | 0.69 | 0.75 | 0.70 | 0.78 | 0.69 |
| TERGITOL TMN 10 | 1.77 | 0.55 | 1.00 | 0.55 | 0.62 | 0.55 |
| Tripropylene glycol | 16.05 | 4.98 | 7.00 | 5.04 | 5.64 | 4.98 |
| Cotton Performance | | | | | | |
| Water Drop | 5 | 4 | 3 | 4 | 4 | 4 |
| Oil Drop | 0 | 0 | 0 | 0 | 0 | 0 |
| Spray | 100 | 85 | 100 | 100 | 80 | 85 |
| Polyester Performance | | | | | | |
| Water Drop | 4 | 4 | 3 | 4 | 4 | 4 |
| Oil Drop | 0 | 0 | 0 | 0 | 0 | 0 |
| Spray | 80 | 70 | 85 | 70 | 70 | 70 |

Polymer compounds of Examples 5-10 exhibited good water repellency by water drop and spray rating methods, regardless of the comonomers present.

Examples 11

A 4-neck 500 mL round bottom flask was set-up with an additional funnel, thermocouple, mechanical stirrer, a nitrogen inlet, condenser, and gas outlet. The flask was charged with sorbitan trioleate methacrylate (53.5 g, 30 wt %) and 125 g of MIBK. The solution was sparged with nitrogen for 10 minutes and heated to 65° C. VAZO 67 (3.2 g) was added to the solution, and the reaction mixture was heated to 80° C. and stirred overnight.

In a separate flask, water (150 g), ARMEEN DM-18D (3.53 g), acetic acid (2.22 g), TERGITOL TMN 10 (1.77 g) and dipropylene glycol (16.05 g) were heated to 70° C. The dispersion water/surfactants was added to the flask and stirred for 30 minutes at 70° C. The dispersion was then homogenized 4 passes at 4000 psi. MIBK was removed via distillation. The final product was filtered through a sock filter. The product contained 17% solids. Dispersions were applied to fabric samples at a rate of 90 g/L at 20% solids, or 3.6 g of polymer per 200 g of pad bath, with 5 g/L of PHOBOL XAN, and tested according to the test methods above.

TABLE 4

Performance of Example 11 on Cotton

| Water Drop | 3 |
|---|---|
| Oil Drop | 0 |
| Spray | 70 |

Example 11 demonstrates that polymers having the trioleate substitution functionality are also effective at providing water repellency.

Example 12

The sorbitan tristearate urethane methacrylate was prepared as described above, at a scale using 25.0 g of sorbitan tristearate. Immediately following the completion of the reaction, the reaction mixture was cooled to 60° C. and 0.90 g of VAZO 67 was added. The reaction was stirred at 80° C. overnight. Warm DI water (114 g), ARMEEN 18D (1.49 g), TERGITOL TMN-10 (1.14 g), acetic acid (1.12 g), and tripropylene glycol (14.6 g) were added to the mixture and stirred for 30 minutes at 70° C. After 30 minutes, the mixture was sonicated. MIBK was removed via distillation, and the product was filtered through a sock filter and diluted to 20.0% solids. Dispersions were applied to fabric samples at a rate of 90 g/L at 20% solids, or 3.6 g of polymer per 200 g of pad bath, and tested according to the test methods above.

Example 13

Example 12 was repeated at a scale using 62.43 g of sorbitan tristearate, except a different surfactant system was used. Warm DI water (284 g), ARMEEN 18D (2.82 g), diacetin (13.76 g), acetic acid (1.76 g), STEPOSOL SB-W (1.06 g), and BRIJ L4 (1.41 g) were added to the mixture and stirred for 30 minutes at 70° C. After 30 minutes, the mixture was homogenized for 4 passes at 6000 psi. MIBK was removed via distillation, and the product was filtered through a sock filter and diluted to 20.0% solids. Dispersions were applied to fabric samples at a rate of 90 g/L at 20% solids, or 3.6 g of polymer per 200 g of pad bath, and tested according to the test methods above.

TABLE 5

Performance of Examples 12-13

| | Example | |
|---|---|---|
| | 12 | 13 |
| Cotton | | |
| Water Drop | 3 | 3 |
| Oil Drop | 0 | 0 |
| Spray | 90 | 100 |
| Polyester | | |
| Water Drop | 3 | 3 |
| Oil Drop | 0 | 0 |
| Spray | 90 | 95 |

Examples 12-13 demonstrate that polymers having a urethane functional group are also effective at providing water repellency.

Examples 14-19

Example 5 was repeated using the reagents listed in Table 6, using 35% by weight monomers, 30% by weight of MIBK, and 35% by weight of isopropyl alcohol cosolvent, except that the reaction mixture was heated to 80° C. overnight, and no PHOBOL XAN was used in the pad bath.

TABLE 6

Reagents and Performance of Examples 14-19

| Example | 14 | 15 | 16 | 17 | 18 | 19 |
|---|---|---|---|---|---|---|
| Reagent Amounts (g) | | | | | | |
| M2 | 28 | 30 | 30 | 30 | 30 | 30 |
| Acrylic Acid | 0.94 | — | — | — | — | — |
| Methacrylic Acid | 0.12 | — | — | — | — | — |
| Diethylamino ethyl methacrylate | — | 5.17 | — | — | — | — |
| BLEMMER PME-400 | 28 | 30 | 30 | 40 | 50 | 15 |
| 7-EO Methacrylate | — | — | — | — | — | 15 |
| VAZO 67 | 1.16 | 1.30 | 1.2 | 1.4 | 1.6 | 1.2 |
| Dispersion Solution (g) | | | | | | |
| Water | 232 | 260.7 | 240.0 | 280.0 | 320.0 | 240.0 |
| Acetic Acid | — | 3.68 | — | — | — | — |
| Diacetin | 10.15 | 26.07 | 24.0 | 28.0 | 32.0 | 24.0 |
| 50 wt % NaOH in water | 2.29 | — | — | — | — | — |
| Cotton Performance | | | | | | |
| Water Drop | 3 | 3.5 | 3 | 3 | 3 | 3 |
| Oil Drop | 0 | 0 | 0 | 0 | 0 | 0 |
| Spray | 80 | 75 | 75 | 80 | 75 | 75 |
| Corn Oil | 4 | 4 | 4 | 4 | 4 | 3.5 |
| Mineral Oil | 4 | 3 | 3 | 3 | 3.5 | 3 |

Examples 14-19 demonstrate the ability of several different copolymers based on a sorbitan tristearate urethane methacrylate to provide water repellency, as well as stain release properties, to a cotton substrate.

Examples 20-22

Example 14 was repeated using the reagents listed in Table 7.

TABLE 7

Reagents and Performance of Examples 20-22

| | Example | | |
|---|---|---|---|
| | 20 | 21 | 22 |
| Reagents (g) | | | |
| M3 | 60 | 28.9 | 28.9 |
| Acrylic Acid | — | 0.95 | — |
| Methacrylic Acid | — | 1.13 | — |
| BLEMMER PME-400 | — | 28.9 | 28.9 |
| VAZO 64 | 1.2 | — | — |
| VAZO 67 | — | 1.20 | 1.16 |
| Surfactant Solution (g) | | | |
| Water | 200 | 239.5 | 231.2 |
| CHEMIDEX S | 1.18 | — | — |
| Acetic Acid | 0.60 | — | — |
| ETHAL LA-4 | 4.21 | — | — |
| STEPOSOL SB-W | 1.00 | — | — |
| Diacetin | 30.59 | 23.95 | 23.12 |
| Stearic Acid | 0.007 | — | — |
| 50 wt % NaOH in water | — | 2.31 | — |
| Cotton Performance | | | |
| Water Drop | 3 | 3 | 3 |
| Oil Drop | 0 | 0 | 0 |
| Spray | 80 | 75 | 75 |
| Corn Oil | | 3 | 3 |
| Mineral Oil | | 1 | 1 |

TABLE 7-continued

Reagents and Performance of Examples 20-22

| | Example | | |
|---|---|---|---|
| | 20 | 21 | 22 |
| Polyester Performance | | | |
| Water Drop | 3 | — | — |
| Oil Drop | 0 | — | — |
| Spray | 75 | — | — |

Examples 20-22 demonstrate that polymers of the invention based on hydrophobically-modified styrene compounds are also effective at providing water repellency.

Examples 23-26

Stock solution of 7-EO methacrylate, N-iso-butoxymethylmethacrylamide, hydroxyethyl methacrylate, and dodecyl mercaptan was prepared at 50% by weight in MIBK according to the amounts in Table 8. Additional monomers and MIBK were combined with stock solution and initiator in a 30-mL vial. The vial was capped and a nitrogen line was connected. Most reactions run at 25-40% solids in MIBK. The reaction was heated to 80° C. overnight. When vinylidene chloride was present, the reaction mixture was instead heated to 50° C. and then temperature was slowly increased to 80° C. (10° C. every 15 minutes) and stirred overnight. Samples were diluted to 10% solids in MIBK, applied to fabric, and tested according to the test methods above.

TABLE 8

Reagents and Performance of Examples 23-26

| | Example | | | |
|---|---|---|---|---|
| | 23 | 24 | 25 | 26 |
| Reagents (g) | | | | |
| M1 | 2.38 | 10.94 | 2.37 | 10.92 |
| 6,2-FMA | 4.00 | — | 4.00 | — |
| 7-EO methacrylate | 0.08 | 0.08 | 0.08 | 0.08 |
| Stearyl methacrylate | 1.00 | — | 1.03 | — |
| N-iso-butoxymethyl methacrylamide | 0.11 | 0.11 | 0.11 | 0.11 |
| Hydroxyethyl methacrylate | 0.09 | 0.09 | 0.09 | 0.09 |
| Dodecyl mercaptan | 0.03 | 0.03 | 0.03 | 0.03 |
| Vinylidene chloride | — | — | 0.72 | 0.67 |
| VAZO 67 | 0.13 | 0.13 | 0.15 | 0.14 |
| Cotton Performance | | | | |
| Water Drop | 9 | 5 | 11 | 4 |
| Oil Drop | 5 | 0 | 6 | 0 |
| Spray | 90 | 90 | 95 | 90 |
| Polyester Performance | | | | |
| Water Drop | 9 | 4 | 9 | 3 |
| Oil Drop | 4 | 1 | 4 | 1 |
| Spray | 95 | 80 | 95 | 85 |

Examples 23-26 demonstrate polymer compositions of the invention tailored to provide both superior water repellency and oil repellency. Excellent oil repellency was observed for partially fluorinated examples.

Examples 27-30

The monomers and initiator were added into a 30 mL vial according to the amounts listed in Table 9. The vial was capped and a nitrogen line was connected. The reaction mixture was heated to 80° C. and stirred overnight. Samples were diluted to 10% solids in MIBK, applied to fabric, and tested according to the test methods above.

TABLE 9

Reagents and Performance of Examples 27-30

| | Example | | | |
|---|---|---|---|---|
| | 27 | 28 | 29 | 30 |
| Reagents (g) | | | | |
| M2 | 2.64 | 11.60 | 2.79 | 12.12 |
| 6,2-FMA | 4.00 | — | 4.00 | — |
| 7-EO methacrylate | 0.08 | 0.08 | 0.08 | 0.08 |
| Stearyl methacrylate | 1.01 | — | 1.03 | — |
| N-iso-butoxymethyl methacrylamide | 0.11 | 0.11 | 0.11 | 0.11 |
| Hydroxyethyl methacrylate | 0.09 | 0.09 | 0.09 | 0.09 |
| Dodecyl mercaptan | 0.03 | 0.03 | 0.03 | 0.03 |
| Vinylidene chloride | | | 0.67 | 0.69 |
| VAZO 67 | 0.13 | 0.13 | 0.15 | 0.14 |
| Cotton Performance | | | | |
| Water Drop | 9 | 4 | 10 | 4 |
| Oil Drop | 5 | 0 | 5 | 0 |
| Spray | 80 | 90 | 90 | 100 |
| Polyester Performance | | | | |
| Water Drop | 9 | 3 | 9 | 3 |
| Oil Drop | 4 | 0 | 4 | 0 |
| Spray | 80 | 90 | 85 | 100 |

Examples 27-30 demonstrate polymer compositions of the invention tailored to provide both superior water repellency and oil repellency.

Examples 31-34

Example 27 was repeated using the reagents of Table 10.

TABLE 10

Reagents and Performance of Examples 31-34

| | Example | | | |
|---|---|---|---|---|
| | 31 | 32 | 33 | 34 |
| Reagents (g) | | | | |
| M2 | 2.77 | 12.74 | 2.77 | 12.73 |
| 6,2-FMA | 4.01 | — | 4.01 | — |
| 7-EO methacrylate | 0.08 | 0.08 | 0.08 | 0.08 |
| Stearyl methacrylate | 1.02 | — | 1.00 | — |
| N-iso-butoxymethyl methacrylamide | 0.11 | 0.11 | 0.11 | 0.11 |
| Hydroxyethyl methacrylate | 0.09 | 0.09 | 0.09 | 0.09 |
| Dodecyl mercaptan | 0.03 | 0.03 | 0.03 | 0.03 |
| Vinylidene chloride | | | 0.66 | 0.67 |
| VAZO 67 | 0.13 | 0.13 | 0.14 | 0.14 |
| Cotton Performance | | | | |
| Water Drop | 10 | 3 | 8 | 4 |
| Oil Drop | 5 | 0 | 4 | 0 |
| Spray | 80 | 80 | 85 | 80 |
| Polyester Performance | | | | |
| Water Drop | 8 | 3 | 6 | 3 |
| Oil Drop | 3 | 0 | 3 | 0 |
| Spray | 100 | 80 | 80 | 80 |

Examples 31-34 demonstrate polymer compositions of the invention tailored to provide both superior water repellency and oil repellency.

Examples 35-40

Example 27 was repeated using the reagents of Table 11.

TABLE 11

Reagents and Performance of Examples 35-40

| Example | 35 | 36 | 37 | 38 | 39 | 40 |
|---|---|---|---|---|---|---|
| Reagent Amounts (g) | | | | | | |
| M1 | 5.34 | 10.68 | — | — | — | — |
| M2 | — | — | 2.96 | 5.92 | — | — |
| M3 | — | — | — | — | 6.23 | 12.45 |
| 6,2-FMA | 3.47 | — | 1.73 | — | 3.47 | — |
| Diethylamino ethyl methacrylate | 1.65 | 1.65 | 0.83 | 0.83 | 1.65 | 1.65 |
| Acrylic Acid | 0.21 | 0.21 | 0.10 | 0.10 | 0.21 | 0.21 |
| Methacrylic Acid | 0.21 | 0.21 | 0.10 | 0.10 | 0.21 | 0.21 |
| VAZO 67 | 0.04 | 0.04 | 0.02 | 0.02 | 0.04 | 0.04 |
| Cotton Performance | | | | | | |
| Water Drop | 6 | 4 | 4 | 4 | 4.5 | 4 |
| Oil Drop | 2 | 0 | 1 | 0 | 1 | 0 |
| Spray | 80 | 90 | 90 | 80 | 80 | 95 |
| Corn Oil | 3 | 1 | 2 | 1 | 2 | 1 |
| Mineral Oil | 3 | 1 | 2 | 1 | 2 | 1 |
| Polyester Performance | | | | | | |
| Water Drop | 4 | 3 | 3 | 3 | 4 | 3 |
| Oil Drop | 2 | 0 | 0 | 0 | 1 | 0 |
| Spray | 75 | 90 | 85 | 80 | 70 | 85 |

Examples 35-40 exhibit the superior water repellency performance of both non-fluorinated and partially-fluorinated polymer compositions of the invention.

Examples 41-46

Example 27 was repeated using the reagents listed in Table 12.

TABLE 12

Reagents and Performance of Examples 41-46

| Example | 41 | 42 | 43 | 44 | 45 | 46 |
|---|---|---|---|---|---|---|
| Reagent Amounts (g) | | | | | | |
| M1 | 2.59 | 12.34 | — | — | — | — |
| M2 | — | — | 2.87 | 9.57 | — | — |
| M3 | — | — | — | — | 3.02 | 10.06 |
| 6,2-FMA | 4.64 | — | 4.64 | — | 4.64 | — |
| Hydroxyethyl methacrylate | 1.1 | 1.1 | 1.1 | 0.77 | 1.1 | 0.77 |
| Stearyl methacrylate | 1.04 | — | 1.04 | — | 1.04 | — |
| VAZO 67 | 0.08 | 0.08 | 0.08 | 0.08 | 0.08 | 0.08 |
| Cotton Performance | | | | | | |
| Water Drop | 9 | 3 | 9 | 3 | 8 | 4 |
| Oil Drop | 4 | 0 | 4.5 | 0 | 4 | 0 |
| Spray | 75 | 75 | 75 | 75 | 75 | 75 |
| Corn Oil | 3 | 1 | 2 | 1 | 2 | 1 |
| Mineral Oil | 3 | 1 | 2 | 1 | 2 | 1 |
| Polyester Performance | | | | | | |
| Water Drop | 5 | 4 | 6 | 3 | 6 | 3 |
| Oil Drop | 3 | 0 | 4 | 0 | 3 | 0 |
| Spray | 80 | 90 | 75 | 80 | 75 | 80 |

Examples 41-46 exhibit the superior water repellency performance of both non-fluorinated and partially-fluorinated polymer compositions of the invention. In this case, stain release properties are boosted by the addition of fluorinated monomers.

Examples 47-52

A 500 mL 4-neck round bottom flask was equipped with a thermocouple, mechanical stirrer, nitrogen inlet, condenser, and gas outlet. The flask was charged with monomers according to Table 14, MIBK (to prepare a 25-40% solution by weight), and tert-butyl alcohol (44.17 g). For Example 44, no MIBK was used, and the amount of tert-butyl alcohol was 85.73 g. The mixture was heated 80° C. and VAZO 67 (0.19 g) was added. The reaction was stirred overnight. Another portion of VAZO 67 (0.19 g) was then added, and the reaction stirred at 80° C. overnight. Warm (65° C.) DI water and sodium chloroacetate (11.17 g) were added to the flask and the mixture was stirred at 82° C. for 2.5 hours. The organic solvent was then removed via rotary evaporation. The product was filtered through a sock filter and diluted to 20% solids. Dispersions were applied to fabric samples at a rate of 90 g/L at 20% solids, or 3.6 g of polymer per 200 g of pad bath, and tested according to the test methods above.

TABLE 14

Reagents and Performance of Examples 47-52

| Example | 47 | 48 | 49 | 50 | 51 | 52 |
|---|---|---|---|---|---|---|
| Reagent Amounts (g) | | | | | | |
| M1 | 9.67 | 38.66 | — | — | — | — |
| M2 | — | — | 10.71 | 42.83 | — | — |
| M3 | — | — | — | — | 11.26 | 45.04 |
| 6,2-FA | 10.00 | — | 10.00 | — | 10.00 | — |
| Dodecyl mercaptan | 2.12 | 2.12 | 2.12 | 2.12 | 2.12 | 2.12 |
| Acrylic acid | 1.15 | 1.15 | 1.15 | 1.15 | 1.15 | 1.15 |
| dimethylamino ethyl methacrylate | 15.2 | 15.2 | 15.2 | 15.2 | 15.2 | 15.2 |
| Butyl acrylate | 1.53 | — | 1.53 | — | 1.53 | — |
| Cotton Performance | | | | | | |
| Water Drop | 1 | 3 | 1 | 3 | 1 | 2 |
| Oil Drop | 0 | 0 | 0 | 0 | 0 | 0 |
| Spray | 50 | 70 | 50 | 70 | 50 | 50 |
| Corn Oil | 3.5 | 2 | 3 | 2 | 2 | 1 |
| Mineral Oil | 3.5 | 1 | 3 | 1 | 2 | 1 |
| Polyester Performance | | | | | | |
| Water Drop | 0 | 3 | 0 | 1 | 0 | 0 |
| Oil Drop | 0 | 0 | 0 | 0 | 0 | 0 |
| Spray | 0 | 60 | 0 | 50 | 0 | 0 |

Examples 47-52 exhibit the water repellency performance on cotton of both non-fluorinated and partially-fluorinated polymer compositions of the invention.

The compounds, compositions, method, and substrates of the present invention are useful to provide excellent water repellency and optionally stain release to treated substrates. The surface properties are obtained using a non-fluorinated or partially fluorinated organic polymer as defined above. The use of non-fluorinated or partially fluorinated organic polymers have been found to provide superior water repellency and durable water repellency compared to traditional non-fluorinated water repellents and are comparable to commercially available fluorinated water repellents.

What is claimed is:

1. A compound of Formula (I):

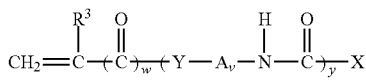
(I)

where
- $R^3$ is selected from H or a $C_1$ to $C_4$ alkyl group;
- Y is selected from O, a substituted arylene group, or an unsubstituted arylene group;
- A is a linear or branched $C_1$ to $C_{10}$ alkylene group;
- w is 0 or 1;
- v is 0 or 1;
- y is 0 or 1;
- provided that w+y is 1 or 2; if w is 0 then Y is a substituted or unsubstituted arylene group; and if Y is O then v is 1;
- X is the residue of a cyclic or acyclic sugar alcohol which is substituted with at least one —$R^1$, —C(O)$R^1$, —$(CH_2CH_2O)_n(CH(CH_3)CH_2O)_mR^2$, —$(CH_2CH_2O)_n(CH(CH_3)CH_2O)_mC(O)R^1$, or mixtures thereof;
- provided that if y is 1, then X is the residue of a cyclic or acyclic sugar alcohol which is substituted with at least two —$R^1$, —C(O)$R^1$, —$(CH_2CH_2O)_n(CH(CH_3)CH_2O)_mC(O)R^1$, or mixtures thereof;
- where the cyclic or acyclic sugar alcohol is selected from a saccharide, reduced sugar, aminosaccharide, aldonic acid, or aldonic acid lactone; wherein
- each n is independently 0 to 20;
- each m is independently 0 to 20;
- m+n is greater than 0;
- each $R^1$ is independently a linear or branched alkyl group having 9 to 29 carbons optionally comprising at least 1 unsaturated bond; and
- each $R^2$ is independently —H, a linear or branched alkyl group having 6 to 30 carbons optionally comprising at least 1 unsaturated bond,
- or mixtures thereof.

2. The compound of claim 1 wherein X is at least 50% bio-based derived.

3. The compound of claim 1 wherein X is 100% bio-based derived.

4. The compound of claim 1 wherein X is selected from Formulas (IIa), (IIb), or (IIc):

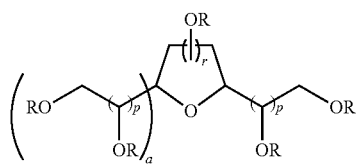
(IIa)

(IIb)
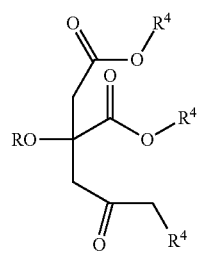

(IIc)

wherein each R is independently a direct bond to C=O of Formula I, —H, —$R^1$, —C(O)$R^1$, —$(CH_2CH_2O)_n(CH(CH_3)CH_2O)_mR^2$, or —$(CH_2CH_2O)_n(CH(CH_3)CH_2O)_mC(O)R^1$;

n and m are defined as above;

m+n is greater than 0;

r is 1 to 3;

a is 0 or 1;

p is independently chosen from 0 to 2;

provided that a is 0 when r is 3;

each $R^1$ and $R^2$ are defined as above;

provided when X is Formula (IIa), then one R is a direct bond to C=O of Formula (I); and at least one R is a —$R^1$, —C(O)$R^1$, —$(CH_2CH_2O)_n(CH(CH_3)CH_2O)_mR^2$, or —$(CH_2CH_2O)_n(CH(CH_3)CH_2O)_mC(O)R^1$;

each $R^4$ is independently a direct bond to C=O of Formula I, —H, a linear or branched alkyl group having 6 to 30 carbons optionally comprising at least 1 unsaturated bond or combinations thereof, —$(CH_2CH_2O)_n(CH(CH_3)CH_2O)_mR^2$, or —$(CH_2CH_2O)_n(CH(CH_3)CH_2O)_mC(O)R^1$;

provided when X is Formula (IIb), then one R or $R^4$ is a direct bond to C=O of Formula (I); and at least one R or $R^4$ is a linear or branched alkyl group optionally comprising at least 1 unsaturated bond or combinations thereof, —$(CH_2CH_2O)_n(CH(CH_3)CH_2O)_mR^2$, or —$(CH_2CH_2O)_n(CH(CH_3)CH_2O)_mC(O)R^1$; and each $R^{19}$ is a direct bond to C=O of Formula I, —H, —C(O)$R^1$, or —$CH_2C[CH_2OR]_3$, provided when X is Formula (IIc), then one $R^{19}$ or R is a direct bond to C=O of Formula I; and at least one $R^{19}$ or R is —C(O)$R^1$, —$(CH_2CH_2O)_n(CH(CH_3)CH_2O)_mR^2$, or —$(CH_2CH_2O)_n(CH(CH_3)CH_2O)_mC(O)R^1$.

5. The compound of claim 4 wherein X is selected from Formula (IIa) to be Formula (IIa'):

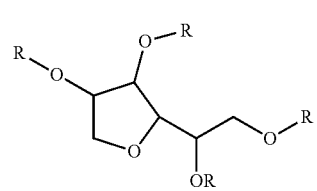
(IIa')

wherein R is further limited to independently a direct bond to C=O, —H, —$R^1$, or —C(O)$R^1$.

6. The compound of claim 4 wherein X is selected from Formula (IIa) to be Formula (IIa'):

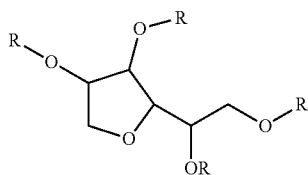
(IIa')

wherein R is further limited to independently a direct bond to C=O, —H, —(CH$_2$CH$_2$O)$_n$(CH(CH$_3$)CH$_2$O)$_m$R$^2$, or —(CH$_2$CH$_2$O)$_n$(CH(CH$_3$)CH$_2$O)$_m$C(O)R$^1$.

7. The compound of claim 4 wherein X is selected from formula (IIb).

8. The compound of claim 4 wherein X is selected from formula (IIc).

9. A composition comprising a mixture of compounds of claim 1.

10. A method of preparing a compound comprising reacting (a) a compound selected from Formula (III)

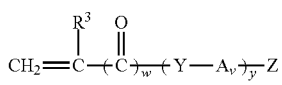
(III)

with (b) at least one cyclic or acyclic sugar alcohol which is substituted with at least one —R$^1$, —C(O)R$^1$, —(CH$_2$CH$_2$O)$_n$(CH(CH$_3$)CH$_2$O)$_m$R$^2$, —(CH$_2$CH$_2$O)$_n$(CH(CH$_3$)CH$_2$O)$_m$C(O)R$^1$, or mixtures thereof;
  provided that if y is 1, then X is the residue of a cyclic or acyclic sugar alcohol which is substituted with at least two —R$^1$, —C(O)R$^1$, —(CH$_2$CH$_2$O)$_n$(CH(CH$_3$)CH$_2$O)$_m$C(O)R$^1$, or mixtures thereof;
  where Y is selected from O, a substituted arylene group, or an unsubstituted arylene group;
  A is a linear or branched C$_1$ to C$_{10}$ alkylene group;
  R$^3$ is selected from H or a C$_1$ to C$_4$ alkyl group;
  w is 0 or 1;
  v is 0 or 1;
  y is 0 or 1;
  Z is selected from a halide, —OC(O)CR$^3$=CH$_2$, —OH, or —NH$_2$ when y is 0 and Z is —NCO when y is 1;
  provided that w+y is 1 or 2; if w is 0 then Y is a substituted or unsubstituted arylene group; and if Y is O then v is 1;
  where the cyclic or acyclic sugar alcohol is selected from a saccharide, reduced sugar, aminosaccharide, aldonic acid, or aldonic acid lactone; wherein
  each n is independently 0 to 20;
  each m is independently 0 to 20;
  m+n is greater than 0;
  each R$^1$ is independently a linear or branched alkyl group having 9 to 29 carbons optionally comprising at least 1 unsaturated bond; and
  each R$^2$ is independently —H, a linear or branched alkyl group having 6 to 30 carbons optionally comprising at least 1 unsaturated bond,
  or mixtures thereof.

11. The method of claim 10, where the at least one cyclic or acyclic sugar alcohol which is substituted is selected from formula (IVa), (IVb), or (IVc):

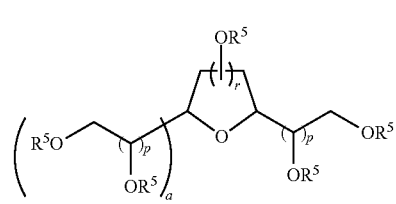
(IVa)

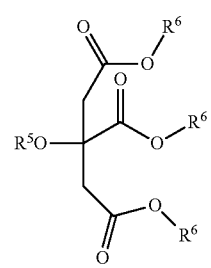
(IVb)

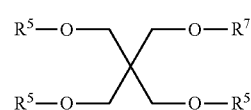
(IVc)

wherein each R$^5$ is independently —H, —R$^1$, —C(O)R$^1$, —(CH$_2$CH$_2$O)$_n$(CH(CH$_3$)CH$_2$O)$_m$R$^2$, or —(CH$_2$CH$_2$O)$_n$(CH(CH$_3$)CH$_2$O)$_m$C(O)R$^1$;
n and m are defined as above;
m+n is greater than 0;
r is 1 to 3;
a is 0 or 1;
p is independently chosen from 0 to 2;
provided that a is 0 when r is 3;
each R$^1$ and R$^2$ are defined as above;
provided when a compound of Formula (IVa) is used, then at least one R$^5$ is a —R$^1$, —C(O)R$^1$, —(CH$_2$CH$_2$O)$_n$(CH(CH$_3$)CH$_2$O)$_m$R$^2$, or —(CH$_2$CH$_2$O)$_n$(CH(CH$_3$)CH$_2$O)$_m$C(O)R$^1$;
each R$^6$ is independently —H, a linear or branched alkyl group having 10 to 30 carbons optionally comprising at least 1 unsaturated bond or combinations thereof, —(CH$_2$CH$_2$O)$_n$(CH(CH$_3$)CH$_2$O)$_m$R$^2$, or —(CH$_2$CH$_2$O)$_n$(CH(CH$_3$)CH$_2$O)$_m$C(O)R$^1$;
provided when a compound of Formula (IVb) is used, then at least one R$^5$ or R$^6$ is a linear or branched alkyl group optionally comprising at least 1 unsaturated bond, or combinations thereof, —(CH$_2$CH$_2$O)$_n$(CH(CH$_3$)CH$_2$O)$_m$R$^2$, or —(CH$_2$CH$_2$O)$_n$(CH(CH$_3$)CH$_2$O)$_m$C(O)R$^1$; and
each R$^7$ is —H, —C(O)R$^1$, or —CH$_2$C[CH$_2$OR$^5$]$_3$,
provided when a compound of Formula (IVc) is used, then at least one R$^7$ or R$^5$ is —C(O)R$^1$, —(CH$_2$CH$_2$O)$_n$(CH(CH$_3$)CH$_2$O)$_m$R$^2$, or —(CH$_2$CH$_2$O)$_n$(CH(CH$_3$)CH$_2$O)$_m$C(O)R$^1$.

12. A polymer compound comprising the repeat unit of Formula (V):

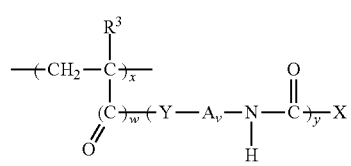
(V)

wherein
R$^3$ is selected from H or a C$_1$ to C$_4$ alkyl group;
x is an integer from 1 to 200;

Y is selected from O, a substituted arylene group, or an unsubstituted arylene group;

A is a linear or branched $C_1$ to $C_{10}$ alkylene group;

w is 0 or 1;

v is 0 or 1;

y is 0 or 1;

provided that w+y is at least 1; if w is 0 then Y is a substituted or unsubstituted arylene group; and if Y is O then v is 1;

X is the residue of a cyclic or acyclic sugar alcohol which is substituted with at least one —$R^1$, —C(O)$R^1$, —($CH_2CH_2O$)$_n$(CH($CH_3$)$CH_2O$)$_m R^2$, —($CH_2CH_2O$)$_n$(CH($CH_3$)$CH_2O$)$_m$C(O)$R^1$, or mixtures thereof;

provided that if y is 1, then X is the residue of a cyclic or acyclic sugar alcohol which is substituted with at least two —$R^1$, —C(O)$R^1$, —($CH_2CH_2O$)$_n$(CH($CH_3$)$CH_2O$)$_m$C(O)$R^1$, or mixtures thereof;

where the cyclic or acyclic sugar alcohol is selected from a saccharide, reduced sugar, aminosaccharide, aldonic acid, or aldonic acid lactone; wherein each n is independently 0 to 20;

each m is independently 0 to 20;

m+n is greater than 0;

each $R^1$ is independently a linear or branched alkyl group having 9 to 29 carbons optionally comprising at least 1 unsaturated bond; and each $R^2$ is independently —H, a linear or branched alkyl group having 6 to 30 carbons optionally comprising at least 1 unsaturated bond, or mixtures thereof.

13. The polymer compound of claim 12, where X is selected from the Formulas (IIa), (IIb), or (IIc):

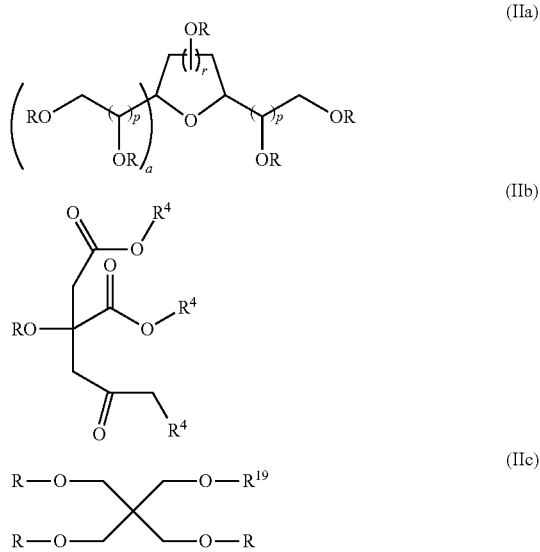

wherein each R is independently a direct bond to C=O of Formula I, —H, —$R^1$, —C(O)$R^1$, —($CH_2CH_2O$)$_n$(CH($CH_3$)$CH_2O$)$_m R^2$, or —($CH_2CH_2O$)$_n$(CH($CH_3$)$CH_2O$)$_m$C(O)$R^1$;

n and m are defined as above;

m+n is greater than 0;

r is 1 to 3;

a is 0 or 1;

p is independently chosen from 0 to 2;

provided that a is 0 when r is 3;

each $R^1$ and $R^2$ are defined as above;

provided when X is Formula (IIa), then one R is a direct bond to C=O of Formula (I); and at least one R is a —$R^1$, —C(O)$R^1$, —($CH_2CH_2O$)$_n$(CH($CH_3$)$CH_2O$)$_m R^2$, or —($CH_2CH_2O$)$_n$(CH($CH_3$)$CH_2O$)$_m$C(O)$R^1$;

each $R^4$ is independently a direct bond to C=O of Formula I, —H, a linear or branched alkyl group having 10 to 30 carbons optionally comprising at least 1 unsaturated bond or combinations thereof, —($CH_2CH_2O$)$_n$(CH($CH_3$)$CH_2O$)$_m R^2$, or —($CH_2CH_2O$)$_n$(CH($CH_3$)$CH_2O$)$_m$C(O)$R^1$;

provided when X is Formula (IIb), then one R or $R^4$ is a direct bond to C=O of Formula (I); and at least one R or $R^4$ is a linear or branched alkyl group optionally comprising at least 1 unsaturated bond or combinations thereof, —($CH_2CH_2O$)$_n$(CH($CH_3$)$CH_2O$)$_m R^2$, or —($CH_2CH_2O$)$_n$(CH($CH_3$)$CH_2O$)$_m$C(O)$R^1$; and each $R^{19}$ is a direct bond to C=O of Formula I, —H, —C(O)$R^1$, or —$CH_2$C[$CH_2$OR]3, provided when X is Formula (IIc), then one $R^{19}$ or R is a direct bond to C=O of Formula I; and at least one $R^{19}$ or R is —C(O)$R^1$, —($CH_2CH_2O$)$_n$(CH($CH_3$)$CH_2O$)$_m R^2$, or —($CH_2CH_2O$)$_n$(CH($CH_3$)$CH_2O$)$_m$C(O)$R^1$.

14. The polymer compound of claim 12 wherein X is at least 50% bio-based derived.

15. The polymer compound of claim 13 wherein X is selected from Formula (IIa) to be Formula (IIa'):

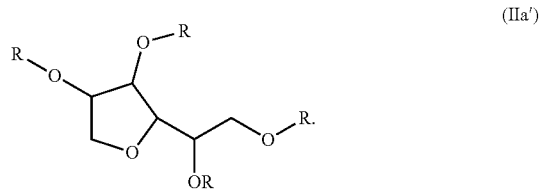

16. The polymer compound of claim 12 further comprising at least one repeat unit from an ethylenically unsaturated monomer having a functional group selected from a linear or branched hydrocarbon, linear or branched fluorocarbon, ether, alcohol, anhydride, oxyalkylene, ester, formate, carboxylic acid, carbamate, urea, amine, amide, sulfonate, sulfonic acid, sulfonamide, halide, saturated or unsaturated cyclic hydrocarbon, morpholine, pyrrolidine, piperidine, or mixtures thereof.

17. The polymer compound of claim 12 further comprising at least one repeat unit from an ethylenically unsaturated monomer selected from linear or branched alkyl (meth)acrylates, amino and diamino (meth)acrylates, linear or branched fluoroalkyl (meth)acrylates optionally interrupted by O, $CH_2$, $CH_2CH_2$, or $SO_2NH$, alkoxylated (meth)acrylates, (meth)acylic acid, vinyl or vinylidene chloride, glycidyl (meth)acrylate, vinyl acetate, hydroxyalkylene (meth)acrylate, urethane or urea (meth)acrylates, (meth)acrylamides including N-methyloyl (meth)acrylamide, alkoxyalkyl (meth)acrylamide, styrene, alpha-methylstyrene, chloromethyl-substituted styrene, ethylenediol di(meth)acrylate, 2-acrylamido-2-methyl-1-propane sulfonic acid (AMPS), and maleic anhydride.

18. A method of treating a fibrous substrate comprising applying to the surface of a substrate a polymer compound of claim 12.

19. The method of claim 18 wherein the contacting is by exhaustion, foam, flex-nip, nip, pad, kiss-roll, beck, skein, winch, liquid injection, overflow flood, roll, brush, roller, spray, dipping or immersion.

20. A substrate treated according to the method of claim 18.

* * * * *